(12) United States Patent
Datta et al.

(10) Patent No.: US 10,973,572 B2
(45) Date of Patent: *Apr. 13, 2021

(54) CATHETER FOR TREATMENT OF ATRIAL FLUTTER HAVING SINGLE ACTION DUAL DEFLECTION MECHANISM

(71) Applicant: Biosense Webster (Israel) Ltd., Yokneam (IL)

(72) Inventors: Keshava Datta, Chino Hills, CA (US); Mario A. Solis, Rancho Cucamonga, CA (US)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 59 days.

This patent is subject to a terminal disclaimer.

(21) Appl. No.: 16/140,484

(22) Filed: Sep. 24, 2018

(65) Prior Publication Data
US 2019/0021791 A1    Jan. 24, 2019

Related U.S. Application Data

(63) Continuation of application No. 15/485,067, filed on Apr. 11, 2017, now Pat. No. 10,080,608, which is a
(Continued)

(51) Int. Cl.
*A61B 18/18*    (2006.01)
*A61M 31/00*    (2006.01)
(Continued)

(52) U.S. Cl.
CPC .......... *A61B 18/1492* (2013.01); *A61B 5/042* (2013.01); *A61M 25/0026* (2013.01);
(Continued)

(58) Field of Classification Search
None
See application file for complete search history.

(56) References Cited

U.S. PATENT DOCUMENTS

| 4,662,404 A | 5/1987 | LeVeen et al. |
| 5,228,441 A | 7/1993 | Lundquist |
| (Continued) | | |

FOREIGN PATENT DOCUMENTS

| JP | 2-109536 A | 4/1990 |
| JP | 07-255855 A | 4/1990 |
| (Continued) | | |

OTHER PUBLICATIONS

Notification of Reasons for Refusal from Japan dated Oct. 18, 2016 for JP Patent Application 2014-560078, English language translation, 5 pages.

(Continued)

*Primary Examiner* — Brian T Gedeon
(74) *Attorney, Agent, or Firm* — Lewis Roca Rothgerber Christie LLP

(57) ABSTRACT

A catheter and method for the treatment of a patient having atrial flutter or other arrhythmia comprises an elongated catheter body having an outer wall, proximal and distal ends, and at least one lumen extending therethrough. Further it has a distal tip section comprising a flexible tubing having a proximal end and a distal end and a plurality of lumens extending therethrough. The proximal end of the tip section is fixedly attached to the distal end of the catheter body. The tip section further comprises a nitinol tube having slots formed therein which causes the distal tip section to deflect using the same puller-wire action used to cause the deflectable catheter to deflect at a point proximal to the distal tip section.

19 Claims, 10 Drawing Sheets

Related U.S. Application Data continuation of application No. 14/973,614, filed on Dec. 17, 2015, now Pat. No. 9,649,158, which is a continuation of application No. 13/781,521, filed on Feb. 28, 2013, now Pat. No. 9,216,056.

(60) Provisional application No. 61/605,886, filed on Mar. 2, 2012.

(51) Int. Cl.
| | |
|---|---|
| A61M 37/00 | (2006.01) |
| A61M 25/00 | (2006.01) |
| A61B 18/14 | (2006.01) |
| A61M 25/01 | (2006.01) |
| A61B 17/00 | (2006.01) |
| A61B 18/00 | (2006.01) |
| A61B 19/00 | (2006.01) |
| A61B 5/042 | (2006.01) |
| A61B 34/20 | (2016.01) |

(52) U.S. Cl.
CPC .... *A61M 25/0138* (2013.01); *A61M 25/0147* (2013.01); *A61B 2017/00309* (2013.01); *A61B 2017/00323* (2013.01); *A61B 2017/00862* (2013.01); *A61B 2018/00029* (2013.01); *A61B 2018/00136* (2013.01); *A61B 2018/00166* (2013.01); *A61B 2018/00357* (2013.01); *A61B 2018/00577* (2013.01); *A61B 2034/2051* (2016.02); *A61B 2217/007* (2013.01); *A61B 2218/002* (2013.01); *A61M 2025/015* (2013.01)

(56) References Cited

U.S. PATENT DOCUMENTS

| | | | |
|---|---|---|---|
| 5,327,905 | A | 7/1994 | Avitall |
| 5,391,199 | A | 2/1995 | Ben-Haim |
| 5,642,736 | A | 7/1997 | Avitall |
| 5,823,955 | A | 10/1998 | Kuck et al. |
| 5,827,278 | A | 10/1998 | Webster, Jr. |
| 5,964,757 | A | 10/1999 | Ponzi |
| 6,239,724 | B1 | 5/2001 | Doron et al. |
| 6,332,089 | B1 | 12/2001 | Acker et al. |
| 6,484,118 | B1 | 11/2002 | Govari |
| 6,618,612 | B1 | 9/2003 | Acker et al. |
| 6,690,963 | B2 | 2/2004 | Ben-Haim et al. |
| 7,232,422 | B2 | 6/2007 | Gibson et al. |
| 7,276,062 | B2 | 10/2007 | McDaniel et al. |
| 7,402,151 | B2 | 7/2008 | Rosenman et al. |
| 7,623,899 | B2 | 11/2009 | Worley et al. |
| 7,729,742 | B2 | 6/2010 | Govari |
| 8,007,462 | B2 | 8/2011 | Gibson et al. |
| 2003/0114832 | A1 | 6/2003 | Kohler et al. |
| 2004/0068178 | A1 | 4/2004 | Govari |
| 2005/0020974 | A1 | 1/2005 | Noriega et al. |
| 2005/0234436 | A1 | 10/2005 | Baxter et al. |
| 2005/0272975 | A1 | 12/2005 | McWeeney et al. |
| 2007/0032826 | A1 | 2/2007 | Schwartz |
| 2008/0300462 | A1 | 12/2008 | Intoccia et al. |
| 2009/0299344 | A1 | 12/2009 | Lee et al. |
| 2010/0268217 | A1 | 10/2010 | Habib |
| 2011/0054446 | A1 | 3/2011 | Schultz |
| 2011/0251519 | A1 | 10/2011 | Romoscanu |
| 2011/0264089 | A1 | 10/2011 | Zirkle et al. |
| 2011/0270246 | A1 | 11/2011 | Clark et al. |

FOREIGN PATENT DOCUMENTS

| | | |
|---|---|---|
| JP | 2011-229918 A | 11/2001 |
| JP | 2004-275765 A | 10/2004 |
| RU | 2008151150 A | 6/2010 |
| WO | 9605768 A1 | 2/1996 |
| WO | 2007136829 A1 | 11/2007 |
| WO | 2010081187 A1 | 7/2010 |

OTHER PUBLICATIONS

PCT International Search Report for International Application No. PCT/US2013/028562, dated Sep. 27, 2013, 6 pages.
English translation of the FIIP Office action dated Dec. 29, 2016, issued in corresponding Russian application No. 2014139829, 8 pages.
English translation of the Fiip Notification of Favorable Examination, issued in corresponding Russian application No. 2014139829, 2 pages.
Written Opinion of the International Searching Authority dated Sep. 27, 2013, issued in PCT/US2013/028562, 14 pages.
International Preliminary Report on Patentability dated Sep. 2, 2014, issued in PCT/US2013/028562, 15 pages.
Australian Patent Examination Report No. 1 dated Oct. 20, 2016, issued in AU Application No. 2013225794, 4 pages.
Extended European Search Report dated Mar. 11, 2019, issued in EP Application No. 18207208.2, 10 pages.
EP Patent Office action dated Apr. 20, 2016, issued in EP Application No. 13708637.7, 9 pages.
English translation of JP Patent Office action dated Jun. 20, 2017, issued in JP Patent Application No. 2014-560078, 3 pages.
English translation of CN Office action dated Nov. 16, 2016, issued in CN Application No. 201380012244.5, 3 pages.
English translation of CN Office action dated Mar. 15, 2016, issued in CN Application No. 201380012244.5, 4 pages.
Intellectual Property of India Office action dated May 8, 2020, issued in in Application No. 7202/DELNP/2014, with English translation, 5 pages.
Canada Patent Office action dated Oct. 22, 2019, issued in CA Application No. 2865416, 4 pages.
Canada Patent Office action dated Oct. 29, 2018, issued in CA Application No. 2865416, 4 pages.

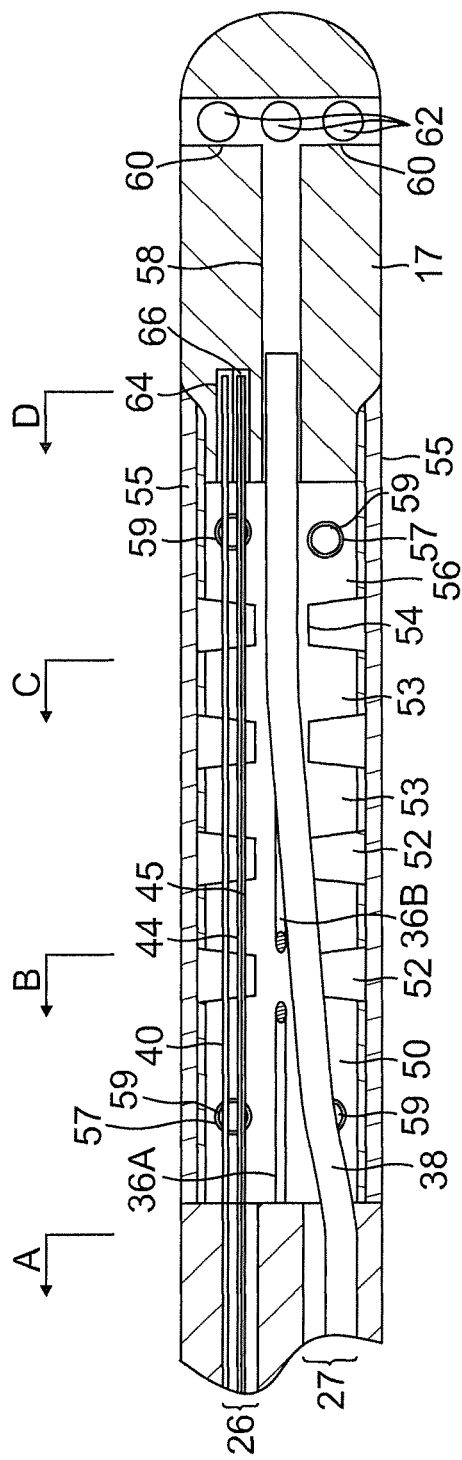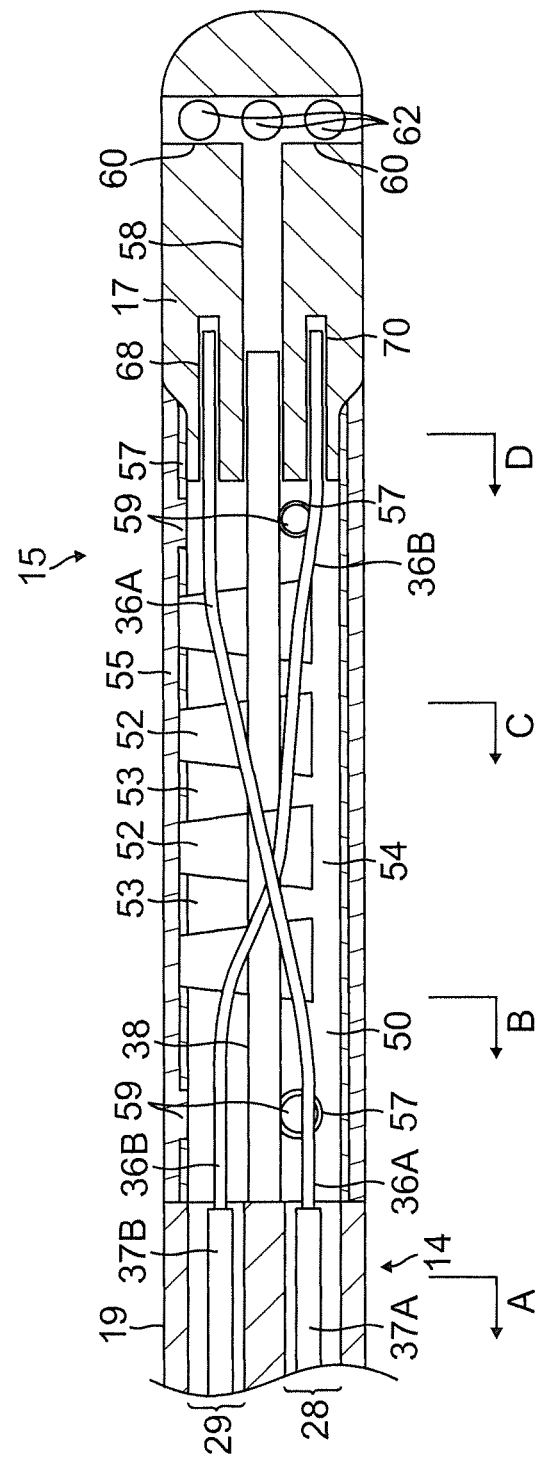
FIG. 5A
FIG. 5B

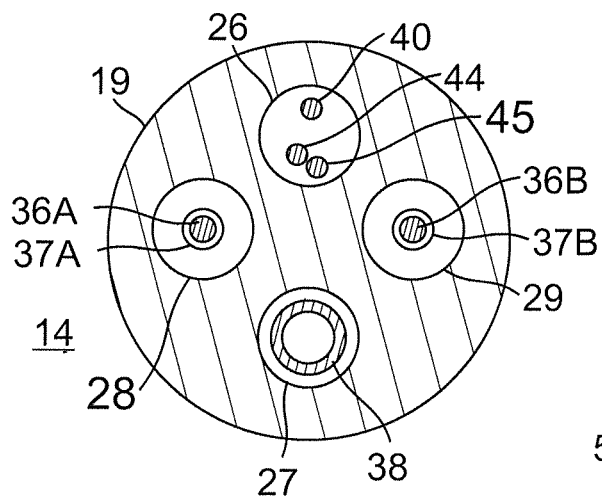
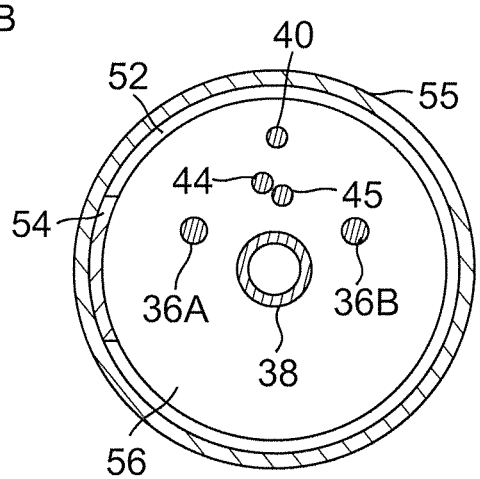
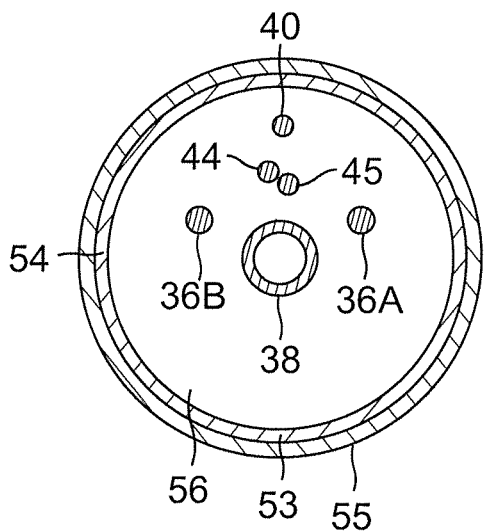
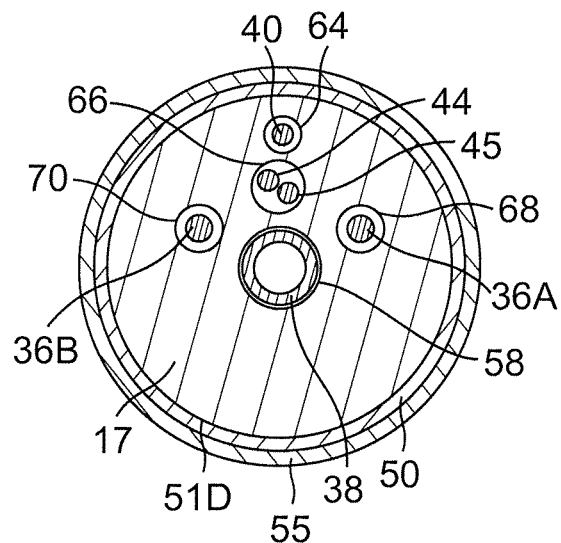
FIG. 6A
FIG. 6B
FIG. 6C
FIG. 6D

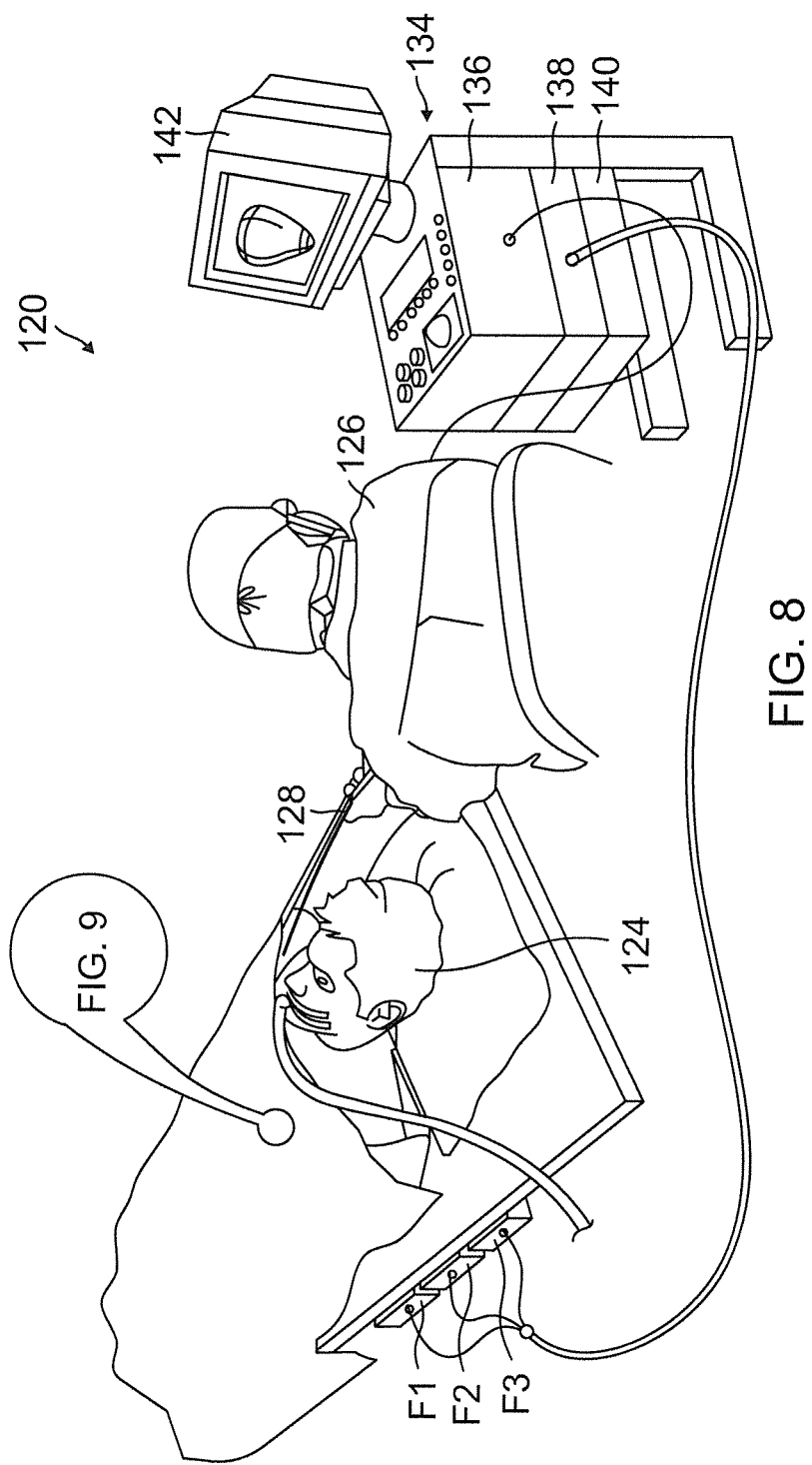

CATHETER FOR TREATMENT OF ATRIAL FLUTTER HAVING SINGLE ACTION DUAL DEFLECTION MECHANISM

CROSS-REFERENCE TO RELATED APPLICATIONS

This application is a continuation of and claims priority to and the benefit of U.S. patent application Ser. No. 15/485,067 filed Apr. 11, 2017, issued as U.S. Pat. No. 10,080,608, which is a continuation of and claims priority to and the benefit of U.S. application Ser. No. 14/973,614 filed Dec. 17, 2015, issued as U.S. Pat. No. 9,649,158, which is a continuation of and claims priority to and the benefit of U.S. application Ser. No. 13/781,521 filed Feb. 28, 2013, issued as U.S. Pat. No. 9,216,056, which claims priority to and the benefit of U.S. Provisional Application Ser. No. 61/605,886, filed Mar. 2, 2012, the entire contents of all of which are incorporated herein by reference.

FIELD OF INVENTION

The present invention relates to a catheter and method of using ablation for the treatment of cardiac arrhythmias, particularly atrial flutter. In particular the catheter and method uses a single action dual deflection mechanism to provide the electrophysiologist with a catheter that is useful in the treatment of cardiac arrhythmias, particularly atrial flutter.

BACKGROUND OF INVENTION

Cardiac arrhythmias, such as atrial flutter and atrial fibrillation in particular, persist as common and dangerous medical ailments, especially in the aging population. In patients with normal sinus rhythm, the heart, which is comprised of atrial, ventricular, and excitatory conduction tissue, is electrically excited to beat in a synchronous, patterned fashion. In patients with cardiac arrythmias, abnormal regions of cardiac tissue do not follow the synchronous beating cycle associated with normally conductive tissue as in patients with normal sinus rhythm. Instead, the abnormal regions of cardiac tissue aberrantly conduct to adjacent tissue, thereby disrupting the cardiac cycle into an asynchronous cardiac rhythm. Such abnormal conduction has been previously known to occur at various regions of the heart, such as, for example, in the region of the sino-atrial (SA) node, along the conduction pathways of the atrioventricular (AV) node and the Bundle of His, or in the cardiac muscle tissue forming the walls of the ventricular and atrial cardiac chambers.

Cardiac arrhythmias, including atrial arrhythmias, may be of a multiwavelet reentrant type, characterized by multiple asynchronous loops of electrical impulses that are scattered about the atrial chamber and are often self propagating. Alternatively, or in addition to the multiwavelet reentrant type, cardiac arrhythmias may also have a focal origin, such as when an isolated region of tissue in an atrium fires autonomously in a rapid, repetitive fashion. Ventricular tachycardia (V-tach or VT) is a tachycardia, or fast heart rhythm that originates in one of the ventricles of the heart. This is a potentially life-threatening arrhythmia because it may lead to ventricular fibrillation and sudden death.

Another type of arrhythmia is atrial flutter (AFL). Atrial flutter is an abnormal heart rhythm that occurs in the atria of the heart. When it first occurs, it is usually associated with a tachycardia and falls into the category of supra-ventricular tachycardia (SVT). While this rhythm occurs most often in individuals with cardiovascular disease or diabetes it may occur spontaneously in people with otherwise normal hearts. It is typically not a stable rhythm, and frequently degenerates into atrial fibrillation (AF). Therefore, treatment of AFL is desirable. Because of the reentrant nature of atrial flutter, it is often possible to ablate the circuit that causes atrial flutter. This is done in the electrophysiology lab by causing a ridge of scar tissue that crosses the path of the circuit that causes atrial flutter. Ablation of the isthmus, as discussed above, is a common treatment for typical atrial flutter. Physicians now a day utilized tip electrodes perpendicular to the tissue during flutter cases and drag the tip over the tissue to ablate linearly, this invention will allowed the physician to position the tip electrode parallel over the tissue with a single pulling action.

Atrial fibrillation occurs when the normal electrical impulses generated by the sinoatrial node are overwhelmed by disorganized electrical impulses that originate in the atria and pulmonary veins causing irregular impulses to be conducted to the ventricles. An irregular heartbeat results and may last from minutes to weeks, or even years. Atrial fibrillation (AF) is often a chronic condition that leads to a small increase in the risk of death often due to strokes. Risk increases with age. Approximately 8% of people over 80 having some amount of AF. Atrial fibrillation is often asymptomatic and is not in itself generally life-threatening, but it may result in palpatations, weakness, fainting, chest pain and congestive heart failure. Stroke risk increases during AF because blood may pool and form clots in the poorly contracting atria and the left atrial appendage. The first line of treatment for AF is medication that either slows the heart rate or revert the heart rhythm back to normal. Additionally, persons with AF are often given anticoagulants to protect them from the risk of stroke. The use of such anticoagulants comes with its own risk of internal bleeding. In some patients, medication is not sufficient and their AF is deemed to be drug-refractory, i.e., untreatable with standard pharmacological interventions. Synchronized electrical cardioversion may also be used to convert AF to a normal heart rhythm. Alternatively, AF patients are treated by catheter ablation. Such ablation is not successful in all patients, however. Thus, there is a need to have an alternative treatment for such patients. Surgical ablation is one option but also has additional risks traditionally associated with surgery.

Diagnosis and treatment of cardiac arrhythmias include mapping the electrical properties of heart tissue, especially the endocardium and the heart volume, and selectively ablating cardiac tissue by application of energy. Such ablation can cease or modify the propagation of unwanted electrical signals from one portion of the heart to another. The ablation process destroys the unwanted electrical pathways by formation of non-conducting lesions. Various energy delivery modalities have been disclosed for forming lesions, and include use of microwave, laser and more commonly, radiofrequency energies to create conduction blocks along the cardiac tissue wall. In a two-step procedure—mapping followed by ablation—electrical activity at points within the heart is typically sensed and measured by advancing a catheter containing one or more electrical sensors (or electrodes) into the heart, and acquiring data at a multiplicity of points. These data are then utilized to select the endocardial target areas at which ablation is to be performed.

Electrode catheters have been in common use in medical practice for many years. They are used to stimulate and map electrical activity in the heart and to ablate sites of aberrant electrical activity. In use, the electrode catheter is inserted into a major vein or artery, e.g., femoral artery, and then guided into the chamber of the heart of concern. A typical ablation procedure involves the insertion of a catheter having a tip electrode at its distal end into a heart chamber. A reference electrode is provided, generally taped to the skin of the patient or by means of a second catheter that is positioned in or near the heart. RF (radio frequency) current is applied to the tip electrode of the ablating catheter, and current flows through the media that surrounds it, i.e., blood and tissue, toward the reference electrode. The distribution of current depends on the amount of electrode surface in contact with the tissue as compared to blood, which has a higher conductivity than the tissue. Heating of the tissue occurs due to its electrical resistance. The tissue is heated sufficiently to cause cellular destruction in the cardiac tissue resulting in formation of a lesion within the cardiac tissue which is electrically non-conductive. During this process, heating of the electrode also occurs as a result of conduction from the heated tissue to the electrode itself. If the electrode temperature becomes sufficiently high, possibly above 60 degrees C., a thin transparent coating of dehydrated blood protein can form on the surface of the electrode. If the temperature continues to rise, this dehydrated layer can become progressively thicker resulting in blood coagulation on the electrode surface. Because dehydrated biological material has a higher electrical resistance than endocardial tissue, impedance to the flow of electrical energy into the tissue also increases. If the impedance increases sufficiently, an impedance rise occurs and the catheter must be removed from the body and the tip electrode cleaned.

SUMMARY OF THE INVENTION

The present invention is directed to a catheter and method for the treatment of patients, particularly, the treatment of cardiac arrhythmias such as atrial flutter and atrial fibrillation using an ablation catheter.

This invention shown herein relates to a single action dual deflection mechanism made possible by a single wire pulling action. During this pulling action, one proximal and one distal deflection are achieved. A catheter is designed with a distal nitinol tube created to collapse under compression force to a desired orientation, allowing a distal deflection of the distal tip section of the catheter using the same puller wire that deflects the catheter at the proximal deflection. Depending on the single puller wire actuated, the proximal deflection is selectively either in the same direction as the distal deflection or in an opposite direction. Within the soft tip structure, a puller wire is attached to the dome electrode, then extends proximally through the nitinol tube and exits through the opposite end of the tube. In one preferred embodiment, each puller wire enters the soft tip lumen in cross-orientation, 180° opposite from puller anchorage (the side of the soft tip where the proximal curve will be formed). The puller wire then travels the length of the catheter to a fixed anchoring point such as the handle piston. Accordingly, the distal end and the proximal end of each puller wire are anchored in diametrically-opposite positions of each other. The catheter is constructed to provide a proximal portion with a greater stiffness and a distal section with a lesser stiffness. As such, the compression force needed to collapse the nitinol tube when the wire is pulled may be lesser than the one require to deflect the soft tip where it is desired that the distal curve is the first one to deflect. Made at a higher pulling force, the proximal curve will be used to access the right atrium walls by the physician giving him control to position the dome electrode and move it during ablation process. The ablation catheter used in the method may include a location sensor such as a magnetic location sensor capable of proving information with regard to the location of the tip of the ablation catheter.

The use a single mechanism to make dual deflection. The present invention minimizes the amount of components to achieve the same results. The catheter has a unique simplicity in construction for a quick dual deflection. Another feature is versatility of the catheter during ablation procedures.

BRIEF DESCRIPTION OF THE DRAWINGS

These and other features and advantages of the present invention will be better understood by reference to the following detailed description when considered in conjunction with the accompanying drawings wherein:

FIG. 5A is a side cross-sectional view of the catheter of FIG. 1, including a junction between the intermediate section and the distal tip section, taken along a first diameter.

FIG. 5B is a side cross-sectional view of the catheter of FIG. 1, including a junction between the intermediate section and the distal tip section, taken along a second diameter generally perpendicular to the first diameter.

FIG. 6A is an end cross-sectional view of the catheter of FIGS. 5A and 5B, taken along line A-A.

FIG. 6B is an end cross-sectional view of the catheter of FIGS. 5A and 5B, taken along line B-B.

FIG. 6C is an end cross-sectional view of the catheter of FIGS. 5A and 5B, taken along line C-C.

FIG. 6D is an end cross-sectional view of the catheter of FIGS. 5A and 5B, taken along line D-D.

FIG. 8 is a schematic, pictorial illustration of a catheter-based medical system, in accordance with an embodiment of the present invention.

DETAILED DESCRIPTION OF THE INVENTION

Figure 1:
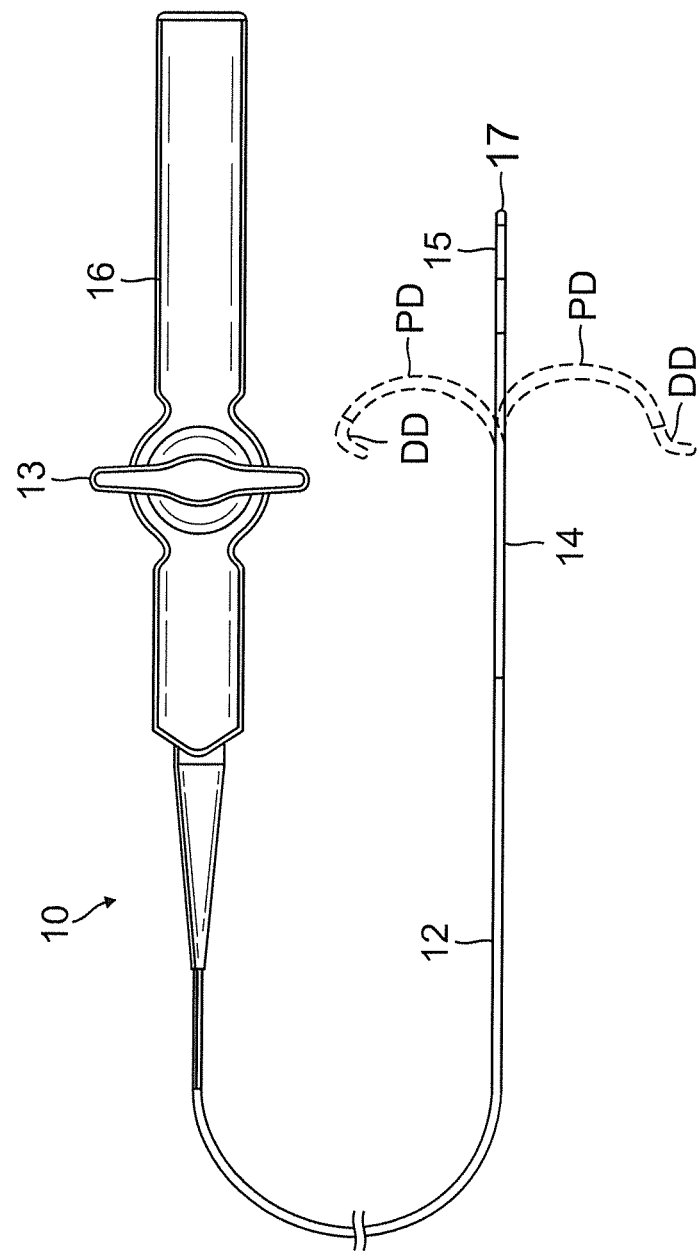
FIG. 1 is a top plan view of a catheter in accordance with an embodiment of the present invention.
Figure 2:
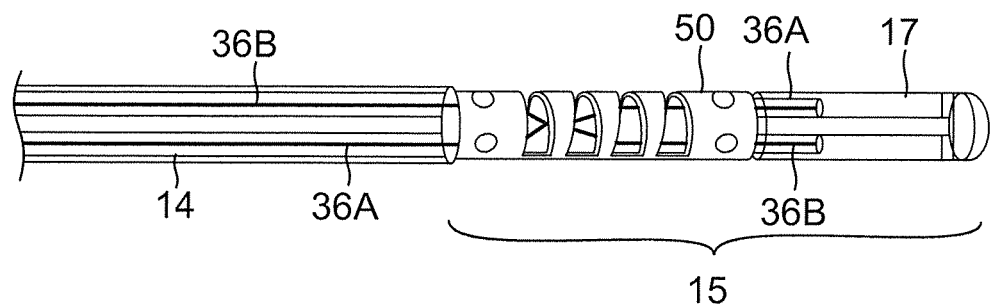
FIG. 2 is a transparent view of a distal tip section of a catheter of FIG. 1, showing puller wires and hinged tube.

With reference to FIGS. 1 and 2, this invention shown and described herein relates to a catheter 10 having an elongated catheter body 12, an intermediate section 14 with bi-directional deflection, a soft distal tip section 15 with uni-directional deflection, and a pair of puller wires 36A and 36B, wherein the catheter 10 provides a single action dual deflection mechanism made possible by a single wire pulling action. During this action, deflection of both the intermediate section 14 and the distal tip section 15 are acquired by a single wire pulling action via a deflection knob 13, where the direction of deflection of the intermediate section 14 (or proximal deflection PD) and the direction of deflection of the distal section 15 (or distal deflection DD) may be the same direction (FIG. 3A) or in opposite directions (FIG. 3B) depending on which single wire is acted on by the user. The soft distal tip section 15 of the catheter is designed with a hinged tube 50 adapted to collapse under compression force to a desired orientation, allowing in the way a predetermined uni-directional distal deflection DD and selective bi-directional proximal deflection BD.

Figure 4A:
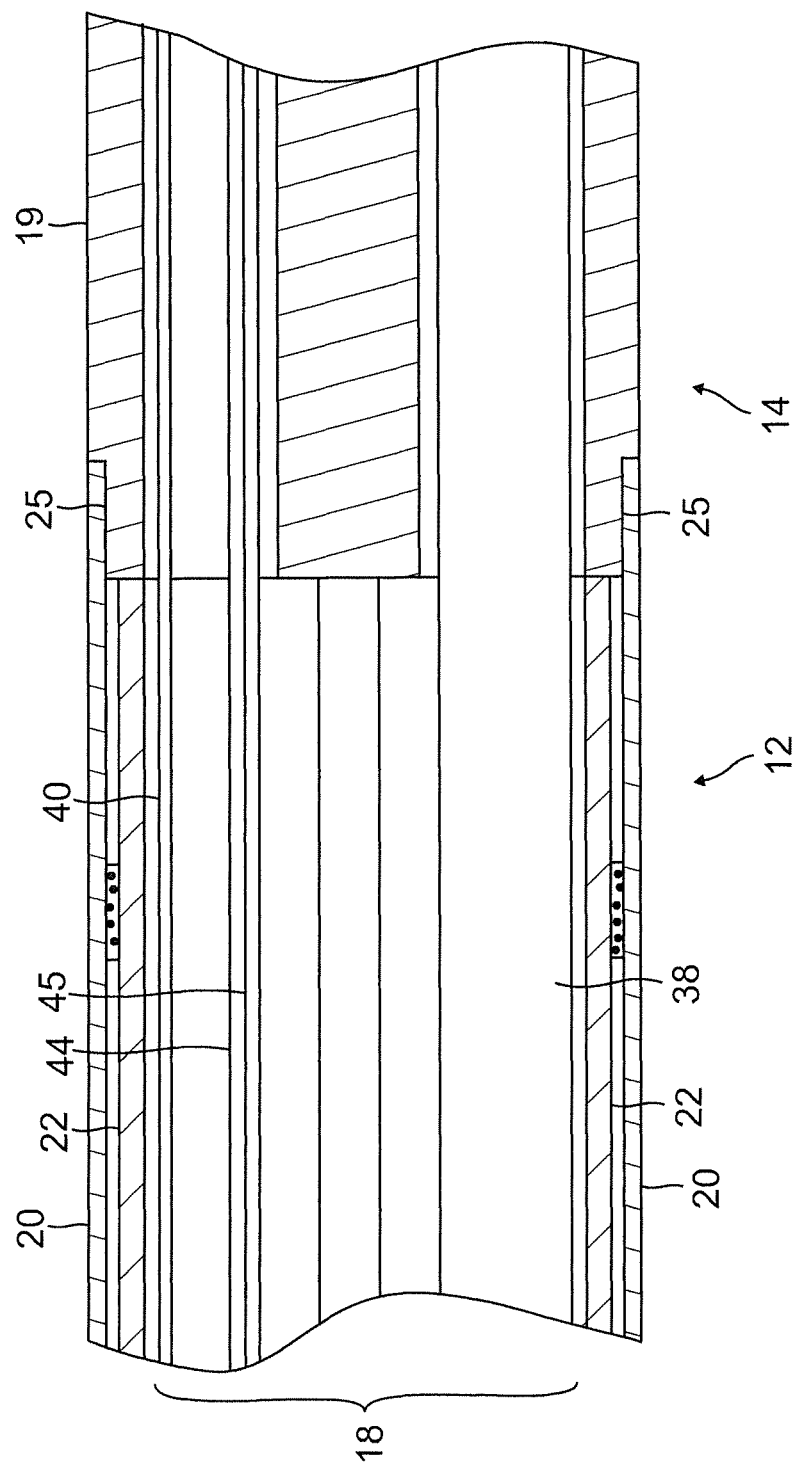
FIG. 4A is a side cross-sectional view of the catheter of FIG. 1, including a junction between a catheter body and an intermediate section, taken along a first diameter.
Figure 4B:
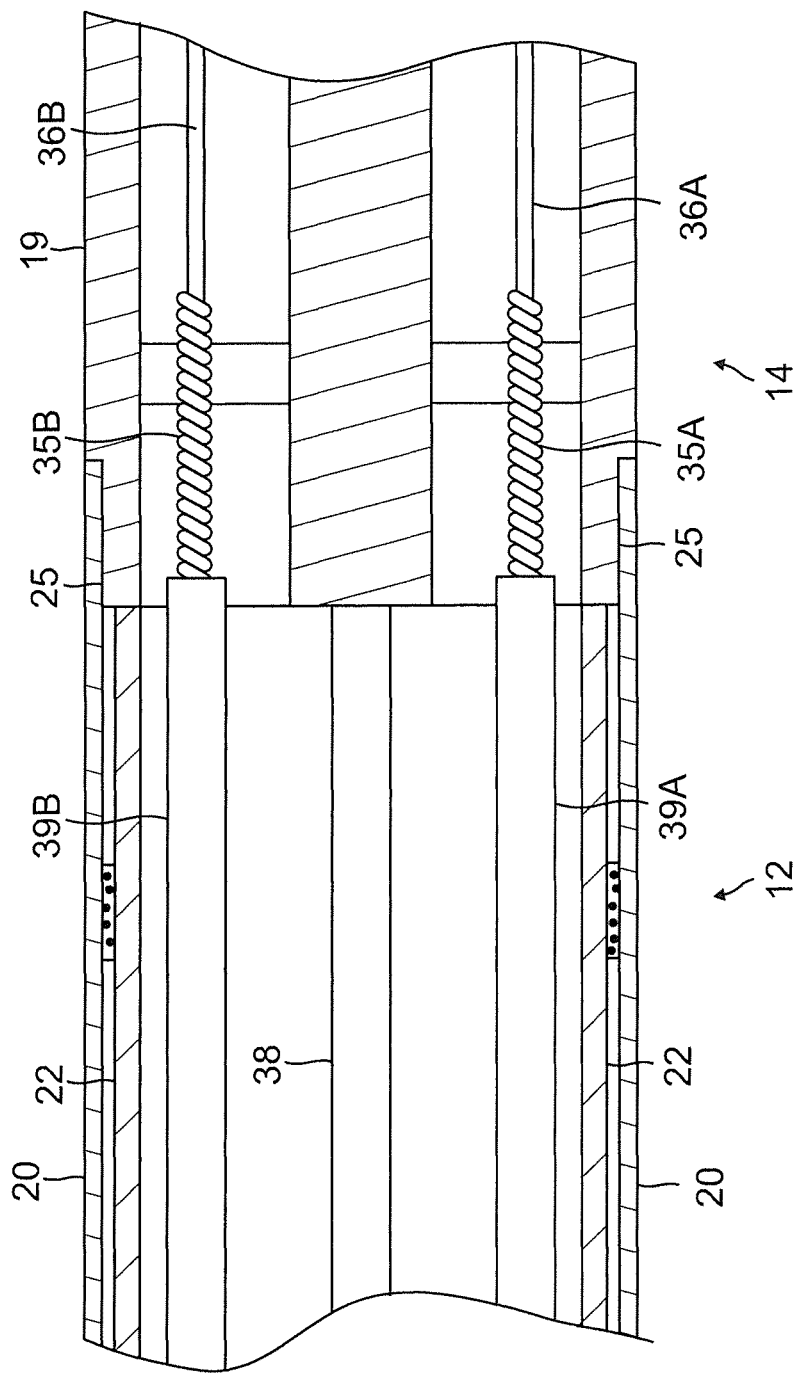
FIG. 4B is a side cross-sectional view of the catheter of FIG. 1, including a junction between a catheter body and an intermediate section, taken along a second diameter generally perpendicular to the first diameter.
Figure 7A:
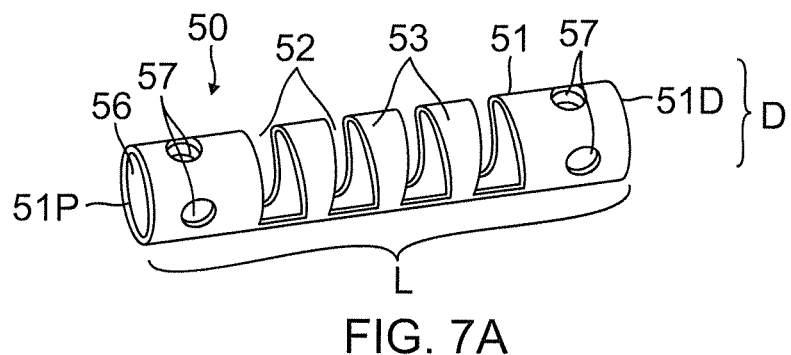
FIG. 7A is a perspective view of a hinged tube, in accordance with an embodiment of the present invention.
Figure 7B:
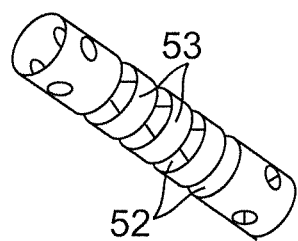
FIG. 7B is another perspective view of the hinged tube of FIG. 7A.
Figure 7C:
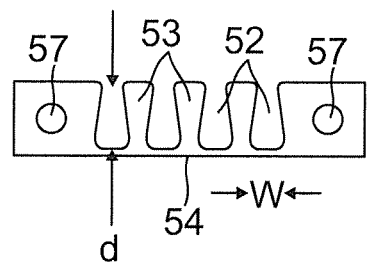
FIG. 7C is a side elevational view of the hinged tube of FIG. 7A.
Figure 7D:
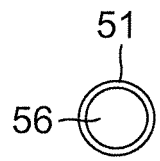
FIG. 7D is an end view of the hinged tube of FIG. 7A.
Figure 7E:
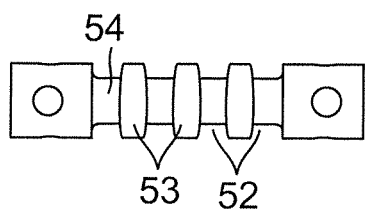
FIG. 7E is a top plan view of the hinged tube of FIG. 7A.
Figure 7F:
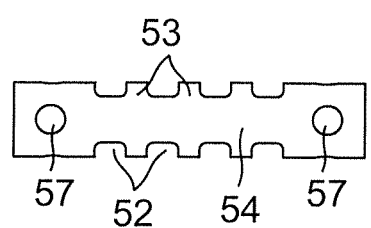
FIG. 7F is a bottom view of the hinged tube of FIG. 7A.

With reference to FIGS. 4A and 4B, the catheter body 12 comprises an elongated tubular construction having a single, axial or central lumen 18. The catheter body is flexible, i.e., bendable, but substantially non-compressible along its length. The catheter body can be of any suitable construction and made of any suitable material. A presently preferred construction comprises an outer wall 20 made of polyurethane or PEBAX. The outer wall may also comprise an imbedded braided mesh of stainless steel or the like to increase torsional stiffness of the catheter body so that, when a control handle 16 is rotated, the intermediate section 14 of the catheter will rotate in a corresponding manner.

The outer diameter of the catheter body is not critical, but is preferably no more than about 8 french, more preferably 7 french. Likewise the thickness of the outer wall is not critical, but is thin enough so that the central lumen can accommodate puller wires, lead wires, and any other desired wires, cables or tubing such as irrigation tubing. If desired, the inner surface of the outer wall 20 is lined with a stiffening tube 22 to provide improved torsional stability Components that extend between the control handle 16 and the deflectable section 14 pass through the central lumen 18 of the catheter body 12. These components include lead wires 40 for a tip dome electrode 17 (and any ring electrodes 21) proximal the tip dome electrode on the distal section 15, an irrigation tubing 38 for delivering fluid to the distal section, puller wire 36A and 36B for causing the proximal and distal deflections and, a pair of thermocouple wires 44 and 45 to sense temperature at the distal tip section 15.

Illustrated in FIGS. 4A and 4B is an embodiment of the intermediate section 14 which comprises a short section of tubing 19. The tubing also has a braided mesh construction but with multiple off-axis lumens, for example lumens 26, 27, 28 and 29. The first lumen 26 carries lead wires 40 for the tip and ring electrodes 17 and 21. The second lumen 27 carries irrigation tubing 38. Each of diametrically-opposed third and fourth lumens 28 and 29 carries a puller wire 36A and 36B. The tubing 19 of the intermediate section 14 is made of a suitable non-toxic material that is more flexible than the catheter body 12. A suitable material for the tubing 19 is braided polyurethane, i.e., polyurethane with an embedded mesh of braided stainless steel or the like. The size of each lumen is not critical, but is sufficient to house the respective components extending therethrough.

A means for attaching the catheter body 12 to the intermediate section 14 is illustrated in FIGS. 4A and 4B. The proximal end of the intermediate section 14 comprises an outer circumferential notch 25 that receives an inner surface of the outer wall 20 of the catheter body 12. The intermediate section 14 and catheter body 12 are attached by glue or the like. If desired, a spacer (not shown) can be located within the catheter body between the distal end of the stiffening tube (if provided) and the proximal end of the intermediate section. The spacer provides a transition in flexibility at the junction of the catheter body and intermediate section, which allows this junction to bend smoothly without folding or kinking. A catheter having such a spacer is described in U.S. Pat. No. 5,964,757, the disclosure of which is incorporated herein by reference.

Each puller wire 36A and 36B is preferably coated with Teflon.® They can be made of any suitable metal, such as stainless steel or Nitinol and the Teflon coating imparts lubricity to the puller wire. Each puller wire preferably has a diameter ranging from about 0.006 to about 0.010 inch.

As illustrated in FIG. 4B, the portion of each puller wire in the catheter body 12 passes through a respective compression coil 35A and 35B in surrounding relation thereto. Each compression coil 35 extends from the proximal end of the catheter body 12 to at or near the proximal end of the intermediate section 14. The compression coils are made of any suitable metal, preferably stainless steel, and are tightly wound on themselves to provide flexibility, i.e., bending, but to resist compression. The inner diameter of the compression coils is preferably slightly larger than the diameter of the puller wires. Within the catheter body 12, the outer surface of each compression coil is also covered by a flexible, non-conductive sheath 39A and 39B, e.g., made of polyimide tubing. The portion of each puller wire distal of the compression coils may extend through a protective plastic sheath (not shown), e.g., of TEFLON.®, to prevent the puller wire from cutting into the tubing 19 of the intermediate section 14 during deflection. Proximal ends of each puller wire are anchored in the control handle 16. Distal ends are anchored in the tip dome electrode 17, as described further below. With reference to FIGS. 5A and 5B, the distal tip section 15 extends from a distal end of the tubing 19 of the intermediate deflectable section 14. The distal tip section 15 includes the hinged tube 50 having a hollow cylindrical body 51 with a lumen 56 a distal end 51D, a proximal end 51P, a length L and a diameter D as shown in FIG. 7A-7F. In accordance with a feature of the present invention, the body has an N plurality of transverse slots 52 defining an (N−1) plurality of hinges 53 therebetween that are generally perpendicular to a spine 54 extending along the length of the body. Each slot 52 (or hinge 53) has a similar depth d and width w. In the illustrated embodiment of FIG. 7C, for each slot, the width w increases with increasing depth d (or stated differently, for each hinge, its width w decreases with increasing depth d). The slots 52 are cut or formed with electrical discharge machining (EDM) or laser machining. A suitable material for construction of the tube is metal and metal alloys, for example, nitinol.

Figure 3A:
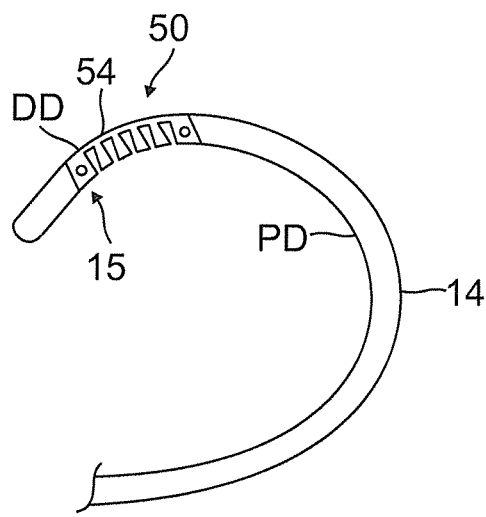
FIG. 3A is a top plan view of the catheter of FIG. 1 depicting dual action deflection with an intermediate section in a proximal deflection and a distal tip section in a distal deflection in the same direction.
Figure 3B:
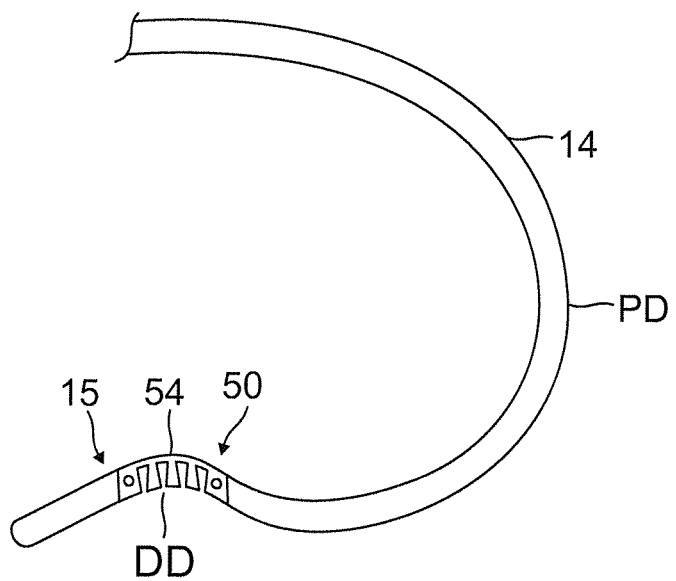
FIG. 3B is a side view of the catheter of FIG. 1 depicting the dual action deflection with an intermediate section in a proximal deflection and a distal tip section in a distal deflection in the opposite direction.

In the illustrated embodiment, the tube 50 has a length ranging between about 0.2 inch and 1.0 inch, with four slots (or three hinges). Advantageously, the configuration or "pitch" of the slots 52 and the hinges 53 (including, plurality, angulation, width and depth) allow the tube 50 to deflect in a predetermined manner in a direction away from the spine 54 when subjected to a compression force, regardless of any other deflection direction along the catheter. When compressed, the hinged tube 50 enables the distal end 51D to deflect in the direction away from the spine between 0 and 90 degrees relative to the proximal end 51P (FIGS. 3A and 3B).

With reference to FIGS. 5A and 5B, the tube 50 is covered with a nonconductive tubing 55 that extends between the distal end of the tubing 19 and a proximal end of the tip dome electrode 17. The tubing 55 may be constructed of a thermoplastic material that can be heated and melted to bond with the tube 50. In that regard, through holes 57 are provided at the distal and proximal ends 51D and 51D of the tube to form nodes 59 that secure the tubing 55 to the tube 50. Alternatively, glue or other adhesives can be applied between the tubing 55 and the tube 50 which form nodes that secure the tubing 55 to the tube 50.

Extending from the lumens of the intermediate deflectable section and through the lumen 56 of the hollow body 51 of the tube 50 are the lead wire 40 for the tip electrode 17, the thermocouple wires 44 and 45, the irrigation tubing 38 and the puller wires 36A and 36B. These components extend further into the tip dome electrode 17.

A proximal end of the tip dome electrode 17 is trepanned to fit within the distal end of the tube 50. A distal end of the tubing 55 fits snugly over the trepanned proximal end of the tip dome electrode 17 to provide a smooth profile as shown in FIGS. 5A and 5B. A proximal surface of the tip dome electrode 17 has a center passage 58 which receives a distal end of the irrigation tubing 38. The passage 58 extends axially through the tip dome electrode 17 and communicates with transverse branches 60 that communicate with irrigation ports 62 leading to outside the tip dome electrode 17. Fluid transported through the irrigation tubing 38 is delivered to the tip dome electrode 17 and outside thereof via the passage 58, transverse branches 60 and ports 62.

The catheter may also have improved irrigation flow through a tip ablation electrode for use in the present method. This catheter is more fully described in U.S. patent application Ser. No. 12/770,582 filed Apr. 29, 2010 which is hereby incorporated by reference. The tip electrode is configured to promote fluid flow into the tip electrode and dispersion of fluid therein in providing more uniform fluid coverage and flow at all locations on the exterior of the tip electrode. The catheter is therefore operable at lower flow rates with lower fluid load on the patient while providing improved cooling of the tip electrode than prior cooling electrodes. Moreover, a high fluid exit velocity at the tip electrode provides a "jetting" action that aids in creating a fluid boundary layer around the tip electrode which reduces the occurrence rate of char and/or thrombus during ablation. Fluid, e.g., saline or heparinized saline, can be transported to the ablation site from the tip electrode to cool tissue, reduce coagulation and/or facilitate the formation of deeper lesions. It is understood that other fluids can be delivered, as well, including any diagnostic and therapeutic fluids, such as neuroinhibitors and neuroexcitors.

The proximal surface of the tip dome electrode 17 also has a plurality of blind holes, including blind hole 64 for receiving the distal end of the tip electrode lead wire 40 and blind hole 66 for the distal ends of the thermocouple wires 44 and 45. There are also blind holes 68 and 70 in which the distal ends of the puller wires 36A and 36B are anchored.

So anchored, each of the puller wires 36A and 36B may be singly actuated by a user through manipulation of the deflection knob 13 (FIG. 1) on the control handle 16 to cause axial force on the puller wire in initially deflecting the distal tip section 15 for a distal deflection DD in a direction away from the spine 54 under a lesser actuation force and subsequently the intermediate section 14 for a proximal deflection PD under a greater actuation force either in the same direction (FIG. 3A), or in an opposition direction (FIG. 3B). Notably, in order for the distal tip section 15 to deflect before the intermediate section 14 deflects when a puller wire is drawn proximally, the distal section 15 (with the tube 50) has a lesser stiffness and the intermediate section 14 has a greater stiffness so that the compression force required to collapse the nitinol tube 50 is lesser than the force required to deflect the intermediate section 14. The proximal deflection PD facilitates access to the right atrium of the heart for the catheter operator and also provides the operator with improved control over the tip dome electrode movement during ablation process.

The blind holes 68 and 70 for anchoring the distal ends of puller wires in the tip dome electrode 17 are diametrically opposed and lie generally in the same plane defined by the diametrically-opposed third and fourth lumens 28 and 29 of the intermediate section 14 through which the puller wires 36A and 36B extend. Although the puller wires 36A and 36B may remain on their respective side of the catheter so as to be axially aligned with their respective lumen in the tubing 19 as they pass through the tube 50 and into the tip dome electrode, a feature of the present invention provides a 180 degree cross-over in the puller wires from one side of the tube 50 to the other side of the tube 50 such that the distal end of each puller wire is anchored diametrically opposite of the proximal end of the puller wire. This cross-over advantageously maintains deflection of the distal tip section 15 to be "on-plane" by reducing the tendency for the distal tip section to twisting during deflection.

This nitinol tube and associated mechanism will allow the tip section to be oriented parallel to the tissue with a single action to deflect the tip.

The distal tip section 15 of the catheter 10 provides many benefits and advantages, including controlled angular deflection, including a proximal deflection and a distal deflection, with a single action Very low force needed to deflect at the distal end due to two deflections accomplished within a single mechanism.

Other embodiments include using a sectional flat blade at the same position where the tube 50 is located within this concept.

This concept can be used with irrigated or non irrigated tip dome electrode.

This concept can also be used in conjunction with a navigation sensor (magnetic sensor) which will be placed below the nitinol tube to avoid shielding.

FIG. 8 is a schematic, pictorial illustration of a conventional system 120 for cardiac catheterization as known in the art. System 120 may be based, for example, on the CARTO.™ system, produced by Biosense Webster Inc. (Diamond Bar, Calif.). This system comprises an invasive probe in the form of a catheter 128 and a control console 134. In the embodiment described hereinbelow, it is assumed that catheter 128 is used in ablating endocardial tissue, as is known in the art. Alternatively, the catheter may be used, mutatis mutandis, for other therapeutic and/or diagnostic purposes in the heart or in other body organs. As shown in FIG. 7, the catheter 28 comprises an elongated catheter body 11, a deflectable intermediate section 12, a distal section 13 carrying at least a tip electrode 15 on its distal tip end 30, and a control handle 16.

Figure 9:
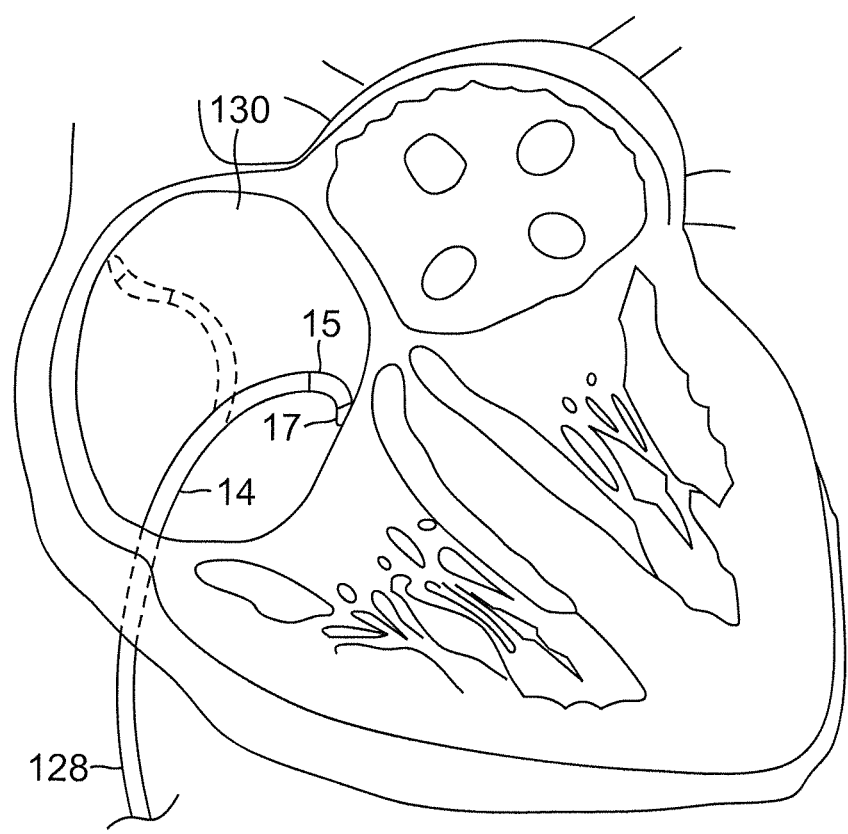
FIG. 9 is a sectional illustration of the catheter of FIG. 8 in use in the right atrium.

An operator 126, such as an interventional cardiologist or electrophysiologist, inserts the catheter 128 of the present invention through the vascular system of a patient so that a distal end of the catheter enters a chamber of the patient's heart, as shown in FIG. 9. The operator advances the catheter so that the distal tip of the catheter engages endocardial tissue at a desired location or locations, including right atrium 130. The catheter is typically connected by a suitable connector at its proximal end to console. The console 134 comprises a radio frequency (RF) generator, which supplies high-frequency electrical energy via the catheter for ablating tissue in the heart at the locations engaged by the distal tip section 15. Alternatively, the catheter and system may be configured to perform ablation by other techniques that are known in the art, such as cryo-ablation, ultrasound ablation or ablation through the use of microwave energy.

Console 134 may also use magnetic position sensing to determine position coordinates of distal end inside the heart of the patient. For this purpose, a driver circuit 138 in console 134 drives field generators F1, F2 and F3 to generate magnetic fields within the body of patient. Typically, the field generators comprise coils, which are placed below the patient's torso at known positions external to the patient. These coils generate magnetic fields in a predefined working volume that contains heart. A magnetic field sensor within distal end of catheter generates electrical signals in response to these magnetic fields. A signal processor processes these signals in order to determine the position coordinates of the distal end section 15, typically including both location and orientation coordinates. This method of position sensing is implemented in the above-mentioned CARTO system and is described in detail in U.S. Pat. Nos. 5,391,199, 6,690,963, 6,484,118, 6,239,724, 6,618,612 and 6,332,089, in PCT Patent Publication WO 96/05768, and in U.S. Patent Application Publications 2002/0065455 A1, 2003/0120150 A1 and 2004/0068178 A1, whose disclosures are all incorporated herein by reference.

A processor in the system typically comprises a general-purpose computer 136, with suitable front end and interface circuits for receiving signals from catheter and controlling the other components of console. The processor may be programmed in software to carry out the functions that are described herein. The software may be downloaded to console in electronic form, over a network, for example, or it may be provided on tangible media, such as optical, magnetic or electronic memory media. Alternatively, some or all of the functions of processor 136 may be carried out by dedicated or programmable digital hardware components. Based on the signals received from the catheter and other components of system, processor drives a display to give operator visual feedback regarding the position of distal end in the patient's body, as well as status information and guidance regarding the procedure that is in progress.

Figure 10B:
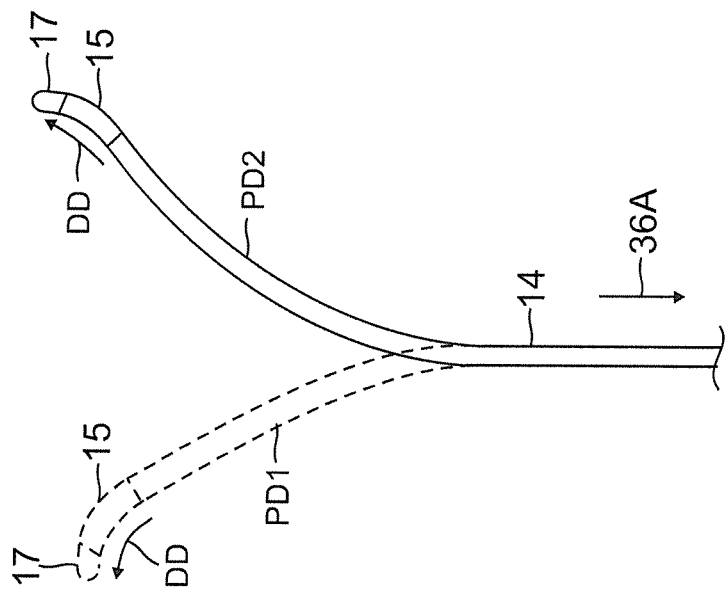
FIG. 10B is a plan view of a catheter in accordance with an embodiment of the present invention, with a uni-directional distal deflection (in full deflection) and a bi-directional proximal deflection (in partial deflection).
Figure 10A:
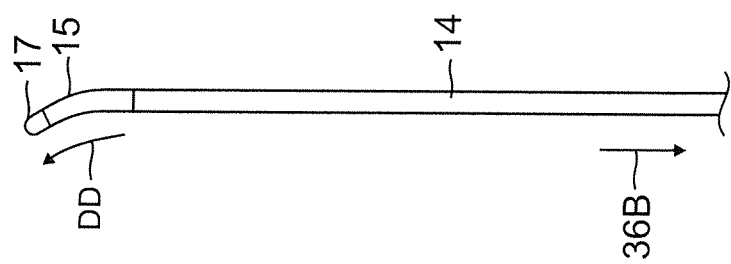
FIG. 10A is a plan view of a catheter in accordance with an embodiment of the present invention, with a distal deflection.

As shown in FIG. 8, the tip dome electrode 17 is placed in contact with tissue in the right atrium 130 by manipulation of the catheter, via the deflection knob 13 of the control handle 16 (FIG. 1) by which the operator 126 draws on a selected puller wire with an initial force to first deflect the distal tip section 15 with a distal deflection DD in a direction away from the spine 54 of the nitinol tube 50 (FIG. 10A). By further drawing on the selected puller wire with a greater force, the intermediate section 14 follows with a proximal deflection which is either in the same direction as the distal deflection or in an opposite direction depending on which single puller wire the operator drew on (FIG. 10B). For example, drawing on puller wire 36B (the puller wire anchored in the tip electrode 17 on the same side as the spine 54) causes a distal deflection DD and a proximal deflection PD1 in the same direction, and drawing on puller wire 36A (the puller wire anchored in the tip electrode oppositely of the spine 54) causes a distal deflection DD and a proximal deflection PD2 in opposite directions.

The electrodes 17 and 21 are constructed of a biocompatible metal, including a biocompatible metal alloy. A suitable biocompatible metal alloy includes an alloy selected from stainless steel alloys, noble metal alloys and/or combinations thereof. In another embodiment, the tip electrode is a shell is constructed of an alloy comprising about 80% palladium and about 20% platinum by weight. In an alternate embodiment, the shell is constructed of an alloy comprising about 90% platinum and about 10% iridium by weight. The shell can formed by deep-drawing manufacturing process which produces a sufficiently thin but sturdy shell wall that is suitable for handling, transport through the patient's body, and tissue contact during mapping and ablation procedures. In a disclosed embodiment, the shell wall has a generally uniform thickness ranging between about 0.003 in and 0.010 in, preferably between about 0.003 in and 0.004 in, and more preferably about 0.0035 in. While the deep drawn method is well suited to manufacturing the shell with a sufficiently thin wall, it is understood that other methods, such as drilling and/or casting/molding, can also be used.

In one irrigated tip electrode there are 56 ports, arranged in six circumferential rows, where five rows R1-R5 have 10 ports each, and a distal row R6 has six ports. The ports of rows R1-R5 are generally equidistant from each other, although the ports of adjacent rows are offset from each other such that each port is equidistant to four or six adjacent ports. A most distal ten-port row R5 is located at the rounded distal portion of the shell. The row (or circle) R6 is on a flat or nearly flat distal end 53 of the shell. The six ports of the row R6 are equi-angular on the circle.

The ring electrodes which are mounted on the connection tubing can be made of any suitable solid conductive material, such as platinum or gold, preferably a combination of platinum and iridium. The ring electrodes can be mounted onto the connection tubing with glue or the like. Alternatively, the ring electrodes can be formed by coating the tubing with an electrically conducting material, like platinum, gold and/or iridium. The coating can be applied using sputtering, ion beam deposition or an equivalent technique. The number of the ring electrodes on the tubing can vary as desired. The rings may be monopolar or bi-polar. In the illustrated embodiment, there is a distal monopolar ring electrode and a proximal pair of bi-polar ring electrodes. Each ring electrode is connected to a respective lead wire. The tip electrode is electrically connected to a source of ablation energy by the lead wire. The ring electrodes are electrically connected to an appropriate mapping or monitoring system by respective lead wires.

For the specific treatment of a cardiac arrhythmia the process is to insert an ablation catheter into the femoral or brachial artery of the patient and to navigate the ablation catheter into a chamber of the heart to perform an ablation of cardiac tissue. In the case of atrial fibrillation or atrial flutter, ablation is performed to achieve isolation of one or more pulmonary veins. The ablation catheter is introduced into an incision an introducer catheter in the femoral artery of the patient and is navigated into the atria of the heart, for example, in accordance with the teachings of United States Patent Publication No. 2007/0032826 by Y. Schwartz entitled "Standardization of Catheter Based Treatments for Atrial Fibrillation". The combination of renal nerve denervation and pulmonary vein isolation provides an improved reduction in the recurrence of atrial fibrillation in patients resulting in a reduction in repeat procedures.

The preceding description has been presented with reference to presently preferred embodiments of the invention. Workers skilled in the art and technology to which this invention pertains will appreciate that alterations and changes in the described structure may be practiced without meaningfully departing from the principal, spirit and scope of this invention. In that regard, the drawings are not necessarily to scale.

Accordingly, the foregoing description should not be read as pertaining only to the precise structures described and illustrated in the accompanying drawings, but rather should be read consistent with and as support to the following claims which are to have their fullest and fair scope.

What is claimed is:

1. A deflectable catheter comprising:
an elongated catheter body having an outer wall, proximal and distal ends, and at least one lumen extending therethrough;
a distal tip section comprising a flexible tubing having a proximal end and a distal end and a plurality of lumens extending therethrough, the proximal end of the tip section being fixedly attached to the distal end of the catheter body, the distal tip section further comprising a nitinol tube having slots formed therein; and
first and second puller wires extending through the elongated catheter body and distal tip section, wherein the nitinol tube and the first and second puller wires are configured such that a single longitudinal movement of either of the first and second puller wires effects both a distal deflection in the distal tip section, and a proximal deflection in the elongated catheter body, the distal deflection being a uni-directional deflection configured to deflect the distal tip section in the same direction whether in response to longitudinal movement of the first puller wire or longitudinal movement of the second puller wire, and the proximal deflection being a selective bi-directional deflection configured to deflect the elongated catheter body in a first direction in response to longitudinal movement of the first puller wire and configured to deflect the elongated body in a second direction in response to longitudinal movement of the second puller wire.

2. A deflectable catheter, comprising:
an elongated catheter body;
a distal tip section having a hinged tube with a spine and at least one slot, the distal tip section configured for distal deflection, the distal tip section having a first stiffness;
an intermediate deflectable section between the catheter body and the distal tip section, the intermediate deflectable section being configured for proximal deflection, the intermediate section having a second stiffness that is greater than the first stiffness;
a tip electrode;
a control handle proximal of the catheter body;
first and second puller wires extending through the catheter body, the intermediate deflectable section and the hinged tube, the first and second puller wires each having a distal end anchored at or near the tip electrode, the first and second puller wires and the hinged tube being configured such that a single longitudinal movement of either of the first and second puller wires effects both the distal deflection of the distal tip section and the proximal deflection of the intermediate deflectable section, the distal deflection of the distal tip section being a uni-directional deflection configured to deflect the distal tip section in the same direction whether in response to longitudinal movement of the first puller wire or longitudinal movement of the second puller wire, and the proximal deflection of the intermediate section being a selective bi-directional deflection configured to deflect the intermediate section in a first direction in response to longitudinal movement of the first puller wire and configured to deflect the intermediate section in a second direction in response to longitudinal movement of the second puller wire.

3. The catheter of claim 2, wherein the proximal and distal deflections are in opposite directions with longitudinal movement of the first puller wire, and the proximal and distal deflections are both in the same direction with longitudinal movement of the second puller wire.

4. The catheter of claim 3, wherein upon longitudinal movement of the first or second puller wire, the distal tip section is deflected before the intermediate deflectable section is deflected.

5. The catheter of claim 2, wherein:
the first puller wire has a first proximal end anchored in the control handle in a first diametrical position, and a first distal end anchored at or near the tip electrode in a second diametrical position that is generally opposite to the first diametrical position of the first proximal end of the first puller wire; and
the second puller wire has a second proximal end anchored in the control handle in a third diametrical position, and a second distal end anchored at or near the tip electrode in a fourth diametrical position that is generally opposite to the third diametrical position of the second proximal end of the second puller wire.

6. The catheter of claim 2, wherein each of the first and second puller wires has about a 180 degree cross-over from one side of the hinged tube to the other side of the hinged tube as it extends through the hinged tube.

7. The catheter of claim 2, wherein the distal tip section further includes a tubing covering the hinged tube.

8. The catheter of claim 7, wherein the tubing is constructed of a thermoplastic material.

9. The catheter of claim 8, wherein the hinged tube has through-holes adapted for receiving nodules formed from the thermoplastic material when heated.

10. The catheter of claim 2, wherein the hinged tube is constructed of nitinol.

11. The catheter of claim 2, wherein the catheter further comprises an irrigation tubing extending from the control handle and into the tip electrode.

12. The catheter of claim 2, wherein the at least one slot has a width that varies with depth.

13. The catheter of claim 2, wherein the at least one slot has a width that increases with depth.

14. The catheter of claim 2, wherein the hinged tube has at least four slots.

15. The catheter of claim 2, wherein upon the single longitudinal movement of either of the first and second puller wires, the distal tip section is deflected before the intermediate deflectable section is deflected.

16. The catheter of claim 2, wherein the intermediate deflectable section includes a multi-lumened tubing.

17. The catheter of claim 16, wherein the multi-lumened tubing has a pair of diametrically opposed lumens, and each of the first and second puller wires extends through a respective one of the pair of diametrically opposed lumens.

18. The catheter of claim 2, wherein the hinged tube is adapted to deflect between about 0 and 90 degrees.

19. The catheter of claim 2, wherein the distal tip section includes a thermoplastic tubing covering the hinged tube.

\* \* \* \* \*